(12) United States Patent
Nafie et al.

(10) Patent No.: US 7,378,283 B2
(45) Date of Patent: May 27, 2008

(54) REACTION MONITORING OF CHIRAL MOLECULES USING FOURIER TRANSFORM INFRARED VIBRATIONAL CIRCULAR DICHROISM SPECTROSCOPY

(75) Inventors: Laurence A. Nafie, Claero, NY (US); Changning Guo, Syracuse, NY (US); Rina K. Dukor, Lake Zurion, IL (US)

(73) Assignee: BioTools, Inc., Jupiter, FL (US)

( * ) Notice: Subject to any disclaimer, the term of this patent is extended or adjusted under 35 U.S.C. 154(b) by 804 days.

(21) Appl. No.: 10/685,319

(22) Filed: Oct. 14, 2003

(65) Prior Publication Data

US 2006/0009919 A1  Jan. 12, 2006

(51) Int. Cl.
*G01N 21/17* (2006.01)

(52) U.S. Cl. ............... 436/171; 356/51; 422/82.05; 422/82.09; 422/82.11; 436/91; 436/103; 436/106; 436/119; 436/124; 436/127; 436/139

(58) Field of Classification Search ............ 356/51, 356/246, 327, 364; 422/68.1, 81, 82.05, 422/82.09, 82.11; 436/52, 86, 91, 103, 106, 436/119, 124, 127, 139, 164–165, 171
See application file for complete search history.

(56) References Cited

U.S. PATENT DOCUMENTS 6,480,277 B1   11/2002   Nafie

OTHER PUBLICATIONS

"Spectroscopic methods for determining enantiomeric purity and absolute configuration in chiral pharmaceutical molecules" by Rekha D. Shah and Laurence A. Nafie, *Current Opinion in Drug Discovery & Development* 4, 764-775 (2001).

"Determination of Enantiomeric Excess in Deuterated Chiral Hydrocarbons by Vibrational Circular Dichroism Spectroscopy" by K.M. Spencer, S.J. Cianciosi, J.E. Baldwin, T.B. Freedman and L.A. Nafie, *Appl. Spectrosc.*, 44, 235-238 (1990).

"Racemization and Geometrical Isomerization of (-)-(R,R)-Cyclopropane 1,2-$^2H_2$" by S.J. Cianciosi, N. Ragunathan, T.B. Freedman, L.A. Nafie, and J.E. Baldwin, *J. Am. Chem. Soc.* 112, 8204-8206 (1990).

Racemization and Geometrical Isomerization of (2S,3S)-Cyclopropane-1-$^{13}$C,$^2$H-2,3-$^2H_2$ at 407 C: Kinetically Competitive One-Center and Two-Center Thermal Epimerizations in an Isotopically Substituted Cyclopropane by S.J. Cianciosi, N. Ragunathan, T.B. Freedman, L. A. Nafie, D.K. Lewis, D.A. Glenar and J.E. Baldwin, *J. Am. Chem. Soc.*, 113, 1864-1866 (1991).

"Analytical Determination of Enantiomeric Purity Using Raman Optical Activity" K. M. Spencer, R. B. Edmonds, R. D. Ruah, M. M. Carrabba, *Anal. Chem.* 6, 1269-1273 (1994).

(Continued)

*Primary Examiner*—Arlen Soderquist
(74) *Attorney, Agent, or Firm*—Barnes & Thornburg LLP (57) ABSTRACT

A method and apparatus to monitor the enantiomeric excess of chiral molecules participating in a chemical reaction. The method includes real time monitoring of the chemical reaction by obtaining a VCD spectra and an IR spectra of the chemical compounds in the reaction, and manipulating the spectra to obtain a % EE value. Using such real time information, the reaction parameters can be changed to shift the reaction to produce more of one chiral molecule than another.

15 Claims, 8 Drawing Sheets

OTHER PUBLICATIONS

"Determination of Enantiomeric Excess using Raman Optical Activity", L. Hecht, A. L. Phillips, L. D. Barron, *J Raman Spectrosc.*, 26, 727-732 (1995).

"Determination of Enantiomeric Purity of Chiral Pharmaceutical Molecules Using Fourier Transform Vibrational Circular Dichroism Spectroscopy" by Laurence A. Nafie, Fujin Long, Henry Buijs, Allan Rilling, Jean-Rene Roy and Rina K. Dukor, Pittcon '97, Atlanta Georgia, Mar. 20, 1997, Abstract #1206.

"The Determination of Enantiomeric Purity by Vibrational Circular Dichroism Spectroscopy" by R.K. Dukor, J.-R. Roy and L.A. Nafie, in *Proceedings of the 12th International Conference on Fourier Transform Spectroscopy*, (Eds. M. Tasumi and K. Itoh), Waseda University Press, Tokyo, Japan, Aug. 23, 1999., p. 263.

"Comparative Evaluation of Vibrational Circular Dichroism and Optical Rotation for Determination of Enantiomeric Purity" C. Zhao, P. L. Polavarapu, *Appl. Spectrosc.*, 55, 913 (2001).

Chen et al., "New design for Fourier transform infrared vibrational circular dichroism spectrometers," *Applied Spectroscopy*, 48(10): 1218-1223 (1994).

Chickos et al., "Thermolysis of (1R,2R)-1,2-Dideuteriocyclobutane. An Application of Vibrational Circular Dichroism to Kinetic Analysis," *Journal of the American Chemical Society*, 108(15): 4398-4402 (1986).

Cianciosi et al., "Racemization and Geometrical Isomerization of (-)-($R_1R$)-Cyclopropane-1,2-2H2," *Journal of the American Chemical Society*, 112(22): 8204-8206 (1990).

Cianciosi et al., "Racemization and geometrical isomerization of (2S,3S)-cyclopropane-1-13C-1,2,3-d3 at 407° C: kenetically competitive one-center and two-center thermal epimerizations in an isotopically substituted cyclopropane," *Journal of the American Chemical Society*, 113(5): 1864-1866 (1991).

Edelmann et al., "Towards functional group-specific detection in high-performance liquid chromatography using mid-infrared quantum cascade lasers," *Journal of Chromatography A*, 934: 123-128 (2001).

Freedman et al., "Kinetics of thermal racemization of (2S,3S)-1-13C-1,2,3-d3-cyclopropane followed by vibrational circular dichroism spectroscopy," *Canadian Journal of Chemistry*, 76(6): 806-810 (1998).

Long et al., "Comparison of step-scan and rapid-scan approaches to the measurement of mid-infrared Fourier transform vibrational circular dichroism," *Applied Spectroscopy*, 51(4): 504-507 (1997).

Setnicka et al., "Sol-gel phase transition of brucine-appended porphyrin gelator: a study by vibrational circular dichroism spectroscopy," *Tetrahedron: Asymmetry*, 13 (24): 2661-2666 (2002).

Shah et al., "Spectroscopic methods for determining enantiometric purity and absolute configuration in chiral pharmaceutical molecules," *Current Opinion in Drug Discovery & Development*, 4(6): 764-775 (2001).

Sivakesava, S et al., "Simultaneous determination of multiple components in lactic acid fermentation using FT-MIR, NIR, and FT-Raman spectroscopic techniques," *Brocess Biochemistry*, 37: 371-378 (2001).

Tran et al., "Chiral Detection in High-Performance Liquid Chromatography by Vibrational Circular Dichroism," *Analytical Chemistry*, 66(17): 2630-2635 (1994).

Urbanova et al., "Measurements of concentration dependence and enantiomeric purity of terpene solutions as a test of a new commercial VCD spectrometer," *Chirality*, 12(4): 199-203 (2000).

Zhao et al., "Comparative evaluation of vibrational circular dichroism and optical rotation for determination of enantiomeric purity," *Applied Spectroscopy*, 55(7): 913-918 (2001).

| Actual EE% | Predicted EE% | Variance (EE%) |
|---|---|---|
| 88.24 | 87.19 | 1.05 |
| 77.78 | 75.89 | 1.89 |
| 68.42 | 69.74 | -1.32 |
| 60.00 | 61.33 | -1.33 |
| 52.38 | 52.16 | 0.22 |
| 45.45 | 45.32 | 0.13 |
| 33.33 | 32.82 | 0.51 |
| 23.08 | 24.39 | -1.31 |
| 14.29 | 15.41 | -1.12 |
| 6.67 | 4.92 | 1.75 |
| 0.00 | 0.27 | -0.27 |
| RMSD | 1.15 ||

|  | Borneol concentration (M) | | | Camphor concentration (M) | | |
| --- | --- | --- | --- | --- | --- | --- |
|  | Actual | Predicted | Variance | Actual | Predicted | Variance |
| 1 | 0.6000 | 0.5982 | -0.0018 | 0.4000 | 0.4018 | 0.0018 |
| 2 | 0.5800 | 0.5794 | -0.0006 | 0.4200 | 0.4206 | 0.0006 |
| 3 | 0.5636 | 0.5639 | 0.0003 | 0.4364 | 0.4361 | -0.0003 |
| 4 | 0.5500 | 0.5502 | 0.0002 | 0.4500 | 0.4498 | -0.0002 |
| 5 | 0.5385 | 0.5398 | 0.0013 | 0.4615 | 0.4602 | -0.0013 |
| 6 | 0.5286 | 0.5276 | -0.0009 | 0.4714 | 0.4724 | 0.0009 |
| 7 | 0.5200 | 0.5206 | 0.0006 | 0.4800 | 0.4794 | -0.0006 |
| 8 | 0.5125 | 0.5144 | 0.0019 | 0.4875 | 0.4856 | -0.0019 |
| 9 | 0.5059 | 0.5044 | -0.0015 | 0.4941 | 0.4956 | 0.0015 |
| 10 | 0.5000 | 0.4994 | -0.0006 | 0.5000 | 0.5006 | 0.0006 |
| RMSD |  | 0.0011 |  |  | 0.0011 |  |

Figure 6

|  | [(1S)-endo]-(-)-Borneol (M) | | | (1S)-(-)-Camphor (M) | | |
| --- | --- | --- | --- | --- | --- | --- |
|  | Actual | Predicted | Variance | Actual | Predicted | Variance |
| 1 | 0.6000 | 0.5837 | -0.0163 | 0.4000 | 0.3891 | -0.0109 |
| 2 | 0.5400 | 0.5372 | -0.0028 | 0.3600 | 0.3581 | -0.0019 |
| 3 | 0.4909 | 0.4814 | -0.0095 | 0.3273 | 0.3210 | -0.0063 |
| 4 | 0.4500 | 0.4473 | -0.0027 | 0.3000 | 0.2982 | -0.0018 |
| 5 | 0.4154 | 0.4129 | -0.0024 | 0.2769 | 0.2753 | -0.0016 |
| 6 | 0.3857 | 0.3851 | -0.0006 | 0.2571 | 0.2567 | -0.0004 |
| 7 | 0.3600 | 0.3655 | 0.0055 | 0.2400 | 0.2437 | 0.0037 |
| 8 | 0.3375 | 0.3407 | 0.0032 | 0.2250 | 0.2271 | 0.0021 |
| 9 | 0.3176 | 0.3219 | 0.0042 | 0.2118 | 0.2146 | 0.0028 |
| 10 | 0.3000 | 0.3150 | 0.0150 | 0.2000 | 0.2100 | 0.0100 |
| RMSD | 0.0081 | | | 0.0054 | | |

Figure 7

|   | EE% of [(1S)-endo]-(-)-borneol | | | EE% of (1S)-(-)-Camphor | | |
|---|---|---|---|---|---|---|
|   | Actual | Predicted | Variance | Actual | Predicted | Variance |
| 1 | 100.00 | 97.57 | -2.43 | 100.00 | 96.84 | -3.16 |
| 2 | 93.10 | 92.71 | -0.39 | 85.71 | 85.15 | -0.56 |
| 3 | 87.10 | 85.37 | -1.73 | 75.00 | 73.60 | -1.40 |
| 4 | 81.82 | 81.29 | -0.53 | 66.67 | 66.29 | -0.37 |
| 5 | 77.14 | 76.50 | -0.64 | 60.00 | 59.82 | -0.18 |
| 6 | 72.97 | 72.98 | 0.01 | 54.55 | 54.35 | -0.20 |
| 7 | 69.23 | 70.21 | 0.98 | 50.00 | 50.83 | 0.83 |
| 8 | 65.85 | 66.23 | 0.38 | 46.15 | 46.77 | 0.61 |
| 9 | 62.79 | 63.81 | 1.02 | 42.86 | 43.29 | 0.44 |
| 10 | 60.00 | 63.07 | 3.07 | 40.00 | 41.95 | 1.95 |
| RMSD | 1.46 | | | 1.32 | | |

Figure 8

REACTION MONITORING OF CHIRAL MOLECULES USING FOURIER TRANSFORM INFRARED VIBRATIONAL CIRCULAR DICHROISM SPECTROSCOPY

FIELD OF INVENTION

The present invention relates to the field of chemical reaction monitoring using spectroscopy and spectrophotometers. Specifically, the invention relates to the field of near-infrared (NIR) and mid-infrared (MIR) spectroscopy and the use of instrumentation to identify chiral molecules and the excess of one enantiomer with respect to another during a reaction.

BACKGROUND OF THE INVENTION

A chiral molecule is a molecule whose mirror image is not superimposable on itself, in the same way that a right and left hand are not superimposable. Monitoring the progress of a chemical reaction, also called reaction monitoring, of chiral molecules involves the measurement of two quantities or properties of the reaction mixture. One quantity is the concentration (amount or fractional composition) of each of the molecular species present in the mixture. This quantity can be determined directly from the absorption spectrum across multiple wavelengths as a function of time during the course of the chemical reaction. The absorption spectrum will relate in some fashion to the concentration of the reacting chemicals. The second property is the percent enantiomeric excess (hereinafter % EE) of each of the chiral molecular species present. The % EE for one chiral molecular species is defined as the difference in concentration of one enantiomer (specific mirror-image form) of a chiral molecule minus that of the opposite enantiomer of the same molecule divided by the total concentration of the molecule (the sum of the concentrations of the two enantiomers) times 100%. The % EE of a single chiral molecular species can be measured using any form of optical activity such as optical rotation (OR) or circular dichroism (CD). When monitoring a chemical reaction of chiral molecular species, it may be desirable to monitor not only the concentration of a compound, but also the % EE of the enantiomers of the compound.

When creating chiral chemical compounds, particularly pharmaceuticals, it may be desirable to create more of a specific enantiomer of the compound and less of another. In such circumstances, it is advantageous to monitor the chemical reaction, so that the maximum of the desired product is produced. In practice, achieving this maximum may require careful management of the reaction conditions and variables, such as pressure, temperature, catalyst and chemical concentrations in the reaction chamber. A variation or change in any one condition could result in less of the desired product being produced.

When preparing to mass produce the compounds, great effort is devoted to determining the optimum conditions. Thus, it is advantageous to know the % EE when devising the conditions at which the production should take place. The method described herein allows real time monitoring of the % EE, allowing the conditions to be adjusted while observing the results of the adjustments. By extension, one will recognize that the % EE monitoring can be used during production to confirm that the proper product is being produced, and that the production is being maximized. If undesirable results are observed, the reaction conditions can be altered to achieve the optimum results. The monitoring methods of the prior art have been insufficient to allow real time monitoring of % EE.

There are two types of spectrometers typically used for measuring circular dichroism (CD), one in the visible and ultraviolet (Vis-UV) regions and another, called Fourier transform vibrational circular dichroism (FT-VCD) in the mid-infrared (MIR) region. OR instruments are also available commercially for fixed single-wavelength points in the Vis-UV region.

CD spectrometers in the Vis-UV regions of the spectrum (14,000 to 50,000 $cm^{-1}$) are based on dispersive instrumentation that requires sequentially scanning the spectrum of interest through all the wavelengths to generate the desired spectrum. However, not all molecules of interest have the electronic transitions in the Vis-UV region as defined above. Additionally, time dependent studies are difficult because of the finite time needed to scan the spectrum, making dispersive techniques unsuitable for real time reaction monitoring.

Another method to monitor the course of a reaction is chiral chromatography. This involves the physical separation of the two enantiomers of the compound which requires time and the expense of maintaining the system including columns and eluting solvents over time. In addition it is not possible to monitor a reaction in real time using chiral chromatography.

CD spectrometers in the MIR region (800 $cm^{-1}$ to 4,000 $cm^{-1}$) of the spectrum are usually based on Fourier transform (FT) spectrometers in which all wavelengths are measured simultaneously. Infrared circular dichroism spectrometers measure the spectra of vibrational transitions of the chemical bonds in the molecules. These spectra, called vibrational circular dichroism (VCD) spectra, possess numerous transitions that are readily interpreted in terms of the structure and conformation of the molecule. Kinetic measurements of chemical reactions made with a FT-VCD spectrometer can be made simultaneously over the entire spectrum during one kinetic experiment, providing a distinct advantage over the dispersive scanning spectrometers, such as CD spectrometers in the Vis-UV region defined above. Thus FT-VCD is suitable for real time reaction monitoring.

The near-infrared (NIR) region of the spectrum lies between the MIR and the Vis-UV regions and spans the frequencies between 4,000 $cm^{-1}$ and 14,000 $cm^{-1}$. The NIR region is attractive because the underlying spectra are based on vibrational transitions and therefore possess the same sensitivity as the MIR region to molecular structure and conformation, as well as possessing a multiplicity of available transitions.

In the prior art, there are no available FT-VCD methods in either the MIR region or the NIR region to monitor the % EE of chiral species during a chemical reaction. Further, there is no indication in the prior art that FT-VCD measurements can be carried out in real time using a flow cell or any other method to monitor simultaneously for all chiral molecular species present the reaction.

The technology of dispersive scanning CD spectrometers is available in Vis-UV. However, it can only be used at one selected wavelength at a time, and thus lacks structural information about the molecule or molecules present. Additionally, if only a single wavelength is available to monitor the progress of a reaction involving two or more chiral molecules, such as with OR or CD in the Vis-UV region, it is not possible to follow simultaneously the % EE of any of the chiral molecules present if there is overlap of the OR or CD of these chiral molecules at that wavelength. The availability of simultaneously obtaining the infrared absorption (FT-IR) and VCD spectra using FT-VCD instrumentation permits the simultaneous determination of % EE of multiple species. The accompanying FT-IR spectrum as a function of time provides the simultaneous determination of the concentration of all chemical species present. When this information is combined with the FT-VCD measurements of the chemical reaction, the % EE of all chiral species present can be obtained by dividing the apparent % EE of each species by its concentration obtained from the ordinary FT-IR spectrum.

The method described herein involves analysis of the reacting species in real time using either a flow cell to bring the reaction mixture into the beam of the analytical instrument or fiber optics to bring the infrared light directly into the vicinity of the reaction vessel with or without the need to move some of the reaction mixture to a flow cell. The % EE of all the chiral species can be monitored simultaneously with the available vibrational FT-IR absorption spectra and FT-VCD spectra by normalizing the contributions of each species present to the VCD spectra by the concentrations of each species present as obtained from the FT-IR absorption spectra.

Early references to % EE determinations using VCD were based on measurements either using a dispersive scanning VCD spectrometer or a FT-VCD spectrometer. Most prior measurements were static, without the use of a flow cell, for a band of frequencies based on first recording the VCD spectrum of the pure enantiomer and then measuring the VCD of a sample that had undergone a chemical reaction or changes in % EE. IR spectra were used to determine the concentration of a single species or reaction product while the magnitude and sign of the VCD intensities could be used to determine the % EE of the enantiomers of the chiral sample molecule. Each of the measurements required a great amount of time to make and analyze. Because of the long scanning time required to measure the VCD spectrum in a dispersive spectrometer, even for one relatively narrow spectral region, there was no opportunity to follow the course of the reaction in time during the course of the reaction. For the FT-VCD measurements of % EE the use of a static cell prevented the possibility of monitoring changes in real time. The present invention allows both at-line and on-line real-time monitoring of continuously changing chemical reactions of chiral species through the use of a flow cell or fiber optic sampling.

Recent comparison of the relative merits of OR and VCD for the determination of % EE, indicate that OR was more accurate than VCD in many cases. However, cases in which either the OR is very small or more than one chiral species is present as a mixture, the % EE determined from the VCD measurement provides definite advantages with reasonable accuracy. In any case, OR is limited to single wavelength chiral monitoring in which it is not possible to follow the % EE of any chiral species, if two or more such species are present, with changing % EE.

BRIEF DESCRIPTION OF THE DRAWINGS

FIG. 3b is a table with the numerical experimental results used to construct the graph in 3a.

FIG. 6 is a table showing the data used to construct the graph of FIG. 5a.

DETAILED DESCRIPTION OF THE PREFERRED EMBODIMENT

One of the simplest applications of VCD is to determine the enantiomeric excess (EE) of a sample consisting of some mixture of enantiomers of a particular chiral molecule. The percent EE (% EE) of a sample is defined as the excess amount of one enantiomer over the other relative to the total concentration of both enantiomers. The expression for the % EE of enantiomer A relative to that of enantiomer B is given by the equation:

$$\% \ EE(A) = (N_A - N_B)100\%/(N_A + N_B) \qquad 1.$$

where $N_A$ is a measure of the moles of enantiomer A and $N_B$ is the corresponding quantity of B. Thus the % EE (A) for an optically pure sample of enantiomer A is 100% while the value for the racemic mixture (50% A and 50% B) is 0%. The value of a pure sample of enantiomer B is −100%.

VCD spectroscopy results in a multiplicity of spectral bands that can be measured simultaneously in the spectrum. These bands serve not only as a measure of vibrational optical activity intensity, but they also carry structural specificity of the chiral molecules being measured, even permitting the simultaneous determination of % EE of more than one chiral species in a given sample.

The magnitude of the VCD spectrum of enantiomer A, or the magnitude of any other form of optical activity, is directly and linearly related to the % EE of enantiomer A. Specifically, the VCD has its maximum value for a sample of 100% EE and is zero for the entire spectrum for the racemic mixture, and is the negative of its maximum value for a sample with −100% EE (a sample of the pure B enantiomer). However, the magnitude of the VCD can also change due to changes in the concentration of the enantiomer.

The method for analysing the % EE of a solution includes providing a reaction involving optically active species and providing an apparatus to permit real time access to the chamber in which the reaction is taking place. This access can be a flow cell, or a fiber optic path from the reaction chamber to the instrumentation. The instrumentation used to practice the method is capable of generating VCD spectra and IR spectra of the material in the reaction chamber.

After obtaining the VCD and IR spectrophotometric measurements, VCD and the IR spectra are decomposed using available statistical program techniques into contributions from each of the species present. The IR contributions of each species present in the mixture are represented as coefficients proportional to the concentration of each species present. The VCD contributions are represented as coefficients proportional to the product of the concentration and the % EE of each chiral species present. If the VCD coefficients are divided by the IR coefficients for each chiral species present, one obtains new VCD coefficients representative of the % EE of each species that are independent of the concentrations of the chiral species present. This completes the analysis of the % EE in the reaction chamber for each present enantiomer. One skilled in the art would know that the determination of the IR and VCD coefficients for each species in a complex mixture can be obtained from spectra of the known IR and VCD spectra for each pure species using available statistical programs. Here the VCD coefficients are apparent coefficients that are related to the true concentration coefficients by multiplication by the fractional EE.

Figure 1:
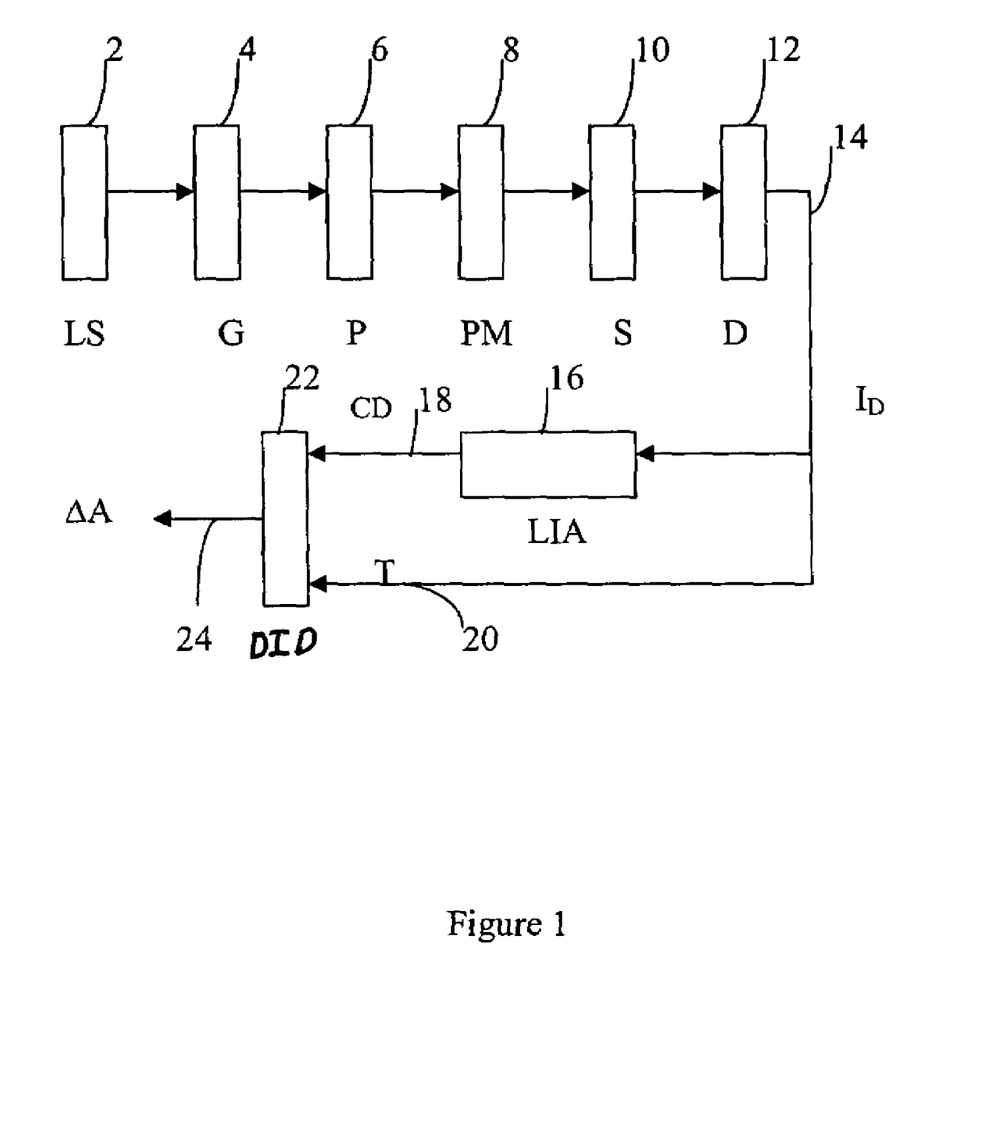
FIG. 1 is a block diagram of an FT-VCD spectrometer.

The optical block diagram of a FT-VCD spectrometer is shown in FIG. 1. The light source (LS) 2 is typically, in the MIR region a special ceramic material that is heated to a given temperature, and in the NIR region is a tungsten halogen lamp. The wavelength selection device (G) 4 is used to identify with Fourier frequencies all wavelengths present in an FT interferometer. A linear polarizer (P) 6 is needed to define a single polarization state such as vertically polarized light. A polarization modulator (PM) 8 switches the polarization between left circular polarized light and right circular polarized light. The sample is placed in a sample position (S) 10. After the light has passed through the above optical components, it is detected at a detector (D) 12. The signal for VCD is isolated and processed by a lock-in amplifier (LIA) 16 and the output signal (CD) 18 is ratioed to the ordinary infrared transmission signal (TR) 20 by division in a computer (DIV) 22 that yields the VCD spectrum ($\Delta A$) 24.

The above description of a basic VCD spectrometer is well known in the prior art and more sophisticated and complex VCD spectrometers are also known. Proof of method experimentation was performed on a dual circular polarization modulated VCD spectrometer available from BioTools, Inc., Wauconda, Ill., USA. The spectrometer is capable of producing both IR and VCD spectra. Both IR and VCD spectra were collected at room temperature with a resolution of 4 $cm^{-1}$ in the spectral range of 800-2000 $cm^{-1}$. A flow cell was used in the sample position 10 with a 0.1 millimeter light path and barium fluoride windows (International Crystal Laboratories, Garfield, N.J., USA). Reaction fluid was pumped through tubing to the flow cell for VCD and IR spectrophotometric measurement.

Experiments were conducted in which known concentrations of a single enantiomer were modified with known concentrations of the opposite enantiomer. Thus the concentrations of both enantiomers in the solution are known at any one time. This simulates a calibration curve for an experimental process and would simulate the reaction itself. The VCD spectrometer was set to measure a series of 24 time blocks of 10-minute measurements. Within that 10-minute block, one minute was used for the IR measurement and nine minutes were used for the VCD measurement. One skilled in the art will recognize that this timing is not necessary to achieve the desired result, as the time needed to acquire a valid spectrum will vary depending upon the spectrometer and composition of the sample being measured.

Figure 2:
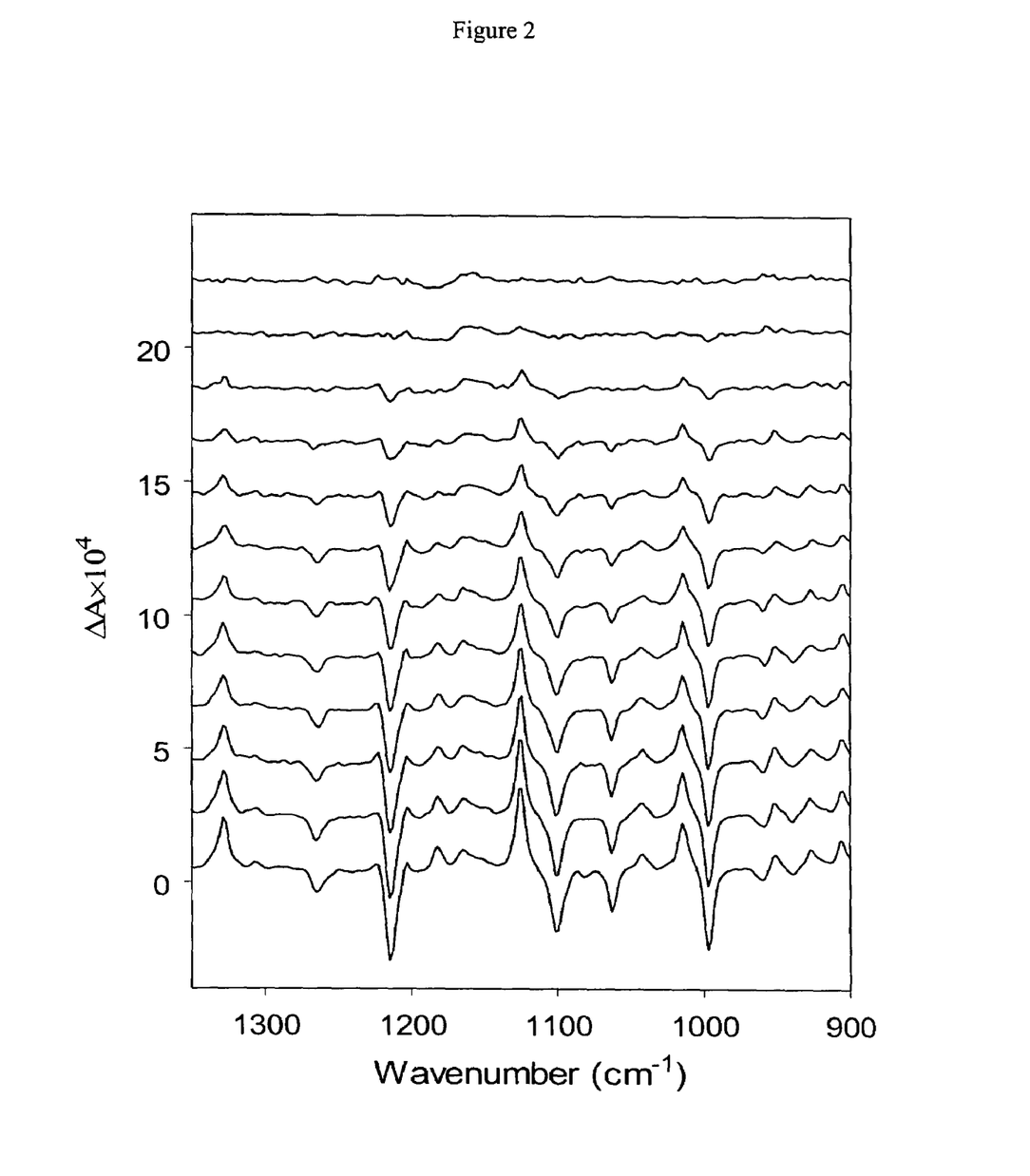
FIG. 2 is a plot of VCD spectra for % EE of 3.14 M (1R)-(+)-α-pinene and 3.14 M (1S)-(−)-α-pinene.
Figure 3A:
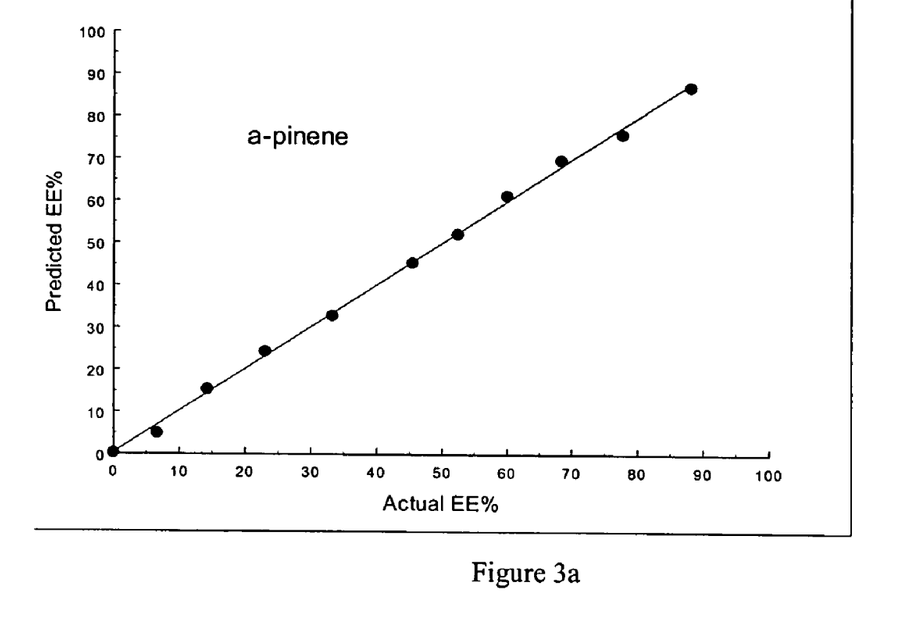
FIG. 3a is a graph showing the predicted % EE versus the actual % EE of α-pinene.
Figure 3B:
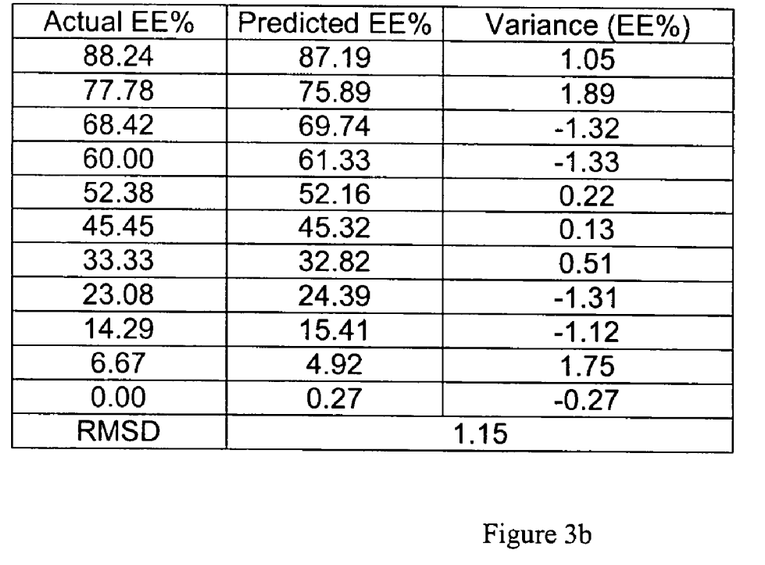

The results of such an experiment are presented in FIG. 2 and FIG. 3. The original solution was 8 milliliters of 3.14 M (1R)-(+)-$\alpha$-pinene in $CCL_4$ obtained from Aldrich Chemical Company and used without further purification. At the beginning of every even numbered time block, the following volumes of 3.14 M (1S)-(−)-$\alpha$-pinene solution 0.5, 0.5, 0.5, 0.5, 0.5, 0.5, 1.0, 1.0, 1.0, 1.0, 1.0, milliliters was injected into the 8 milliliters of the original solution. The results from the odd numbered blocks were analyzed and presented in FIG. 2. The IR spectrum does not change because the concentration of the compound (pinene) does not change. The % EE corresponding to the additions are, (no addition) 100% 40, 88.2% 42, 77.8% 44, 68.4% 46, 60% 48, 52.4% 50, 45.5% 52, 33.3% 54, 23.1% 56, 14.3% 58, 6.7% 60, and 0% 62. The VCD measurement changes from that of pure (1R)-(+)-$\alpha$-pinene to a racemic mixture of pinene. The spectra for the racemic mixture 62 is essentially the background of the instrument system. Thus from measurements of the VCD spectrum at some point in time during the course of a reaction, we could determine the % EE of the solution at that point in time, but this is only because the concentration of pinene did not change. This experiment mimics a reaction in which a solution of pure enantiomer is transformed into a racemic mixture. This type of experiment is known in the prior art.

In an effort to improve the determination of % EE over the conventional method of simply monitoring at a single wavelength or individual scanned peaks, a statistical method know as partial least squares (PLS) was used that simultaneously considers all points in the entire FT-VCD spectrum for statistical analysis. Other statistical analyses, known in the art as chemometrics, could also be used. The PLS analysis was carried out using the software PLSplus/IQ module in Grams/32 AI (6.00) (Galactic Industries, Inc., Salem, N.H., USA). One of the advantages of the PLS analysis is that it can carry out "whole spectra" analysis. Instead of selecting individual peaks, a large spectral region can be used and the unprocessed spectra can be used without solvent-subtraction and baseline correction. In the PLS analysis of the data, spectra containing higher concentrations of the enantiomer are weighted more heavily than those with low concentrations. Thus the PLS method is considered an excellent tool for VCD quantitative analysis. In this experiment, the VCD spectra between 900 $cm^{-1}$ and 1350 $cm^{-1}$ were analyzed. FIG. 3 shows the results from the PLS analysis of this experiment. The abscissa is the actual % EE from the known additions and the ordinate is the calculated % EE using the PLS analysis. The correlation coefficient between the actual concentration of enantiomer and the PLS determined concentration was 0.9984 (1.0000 being perfect). The root-mean-squares deviation of % EE is 1.15% which indicates that the method is accurate to close to one percent. Thus the combination of VCD and PLS analysis can result in accurate analysis of the % EE.

Figure 4:
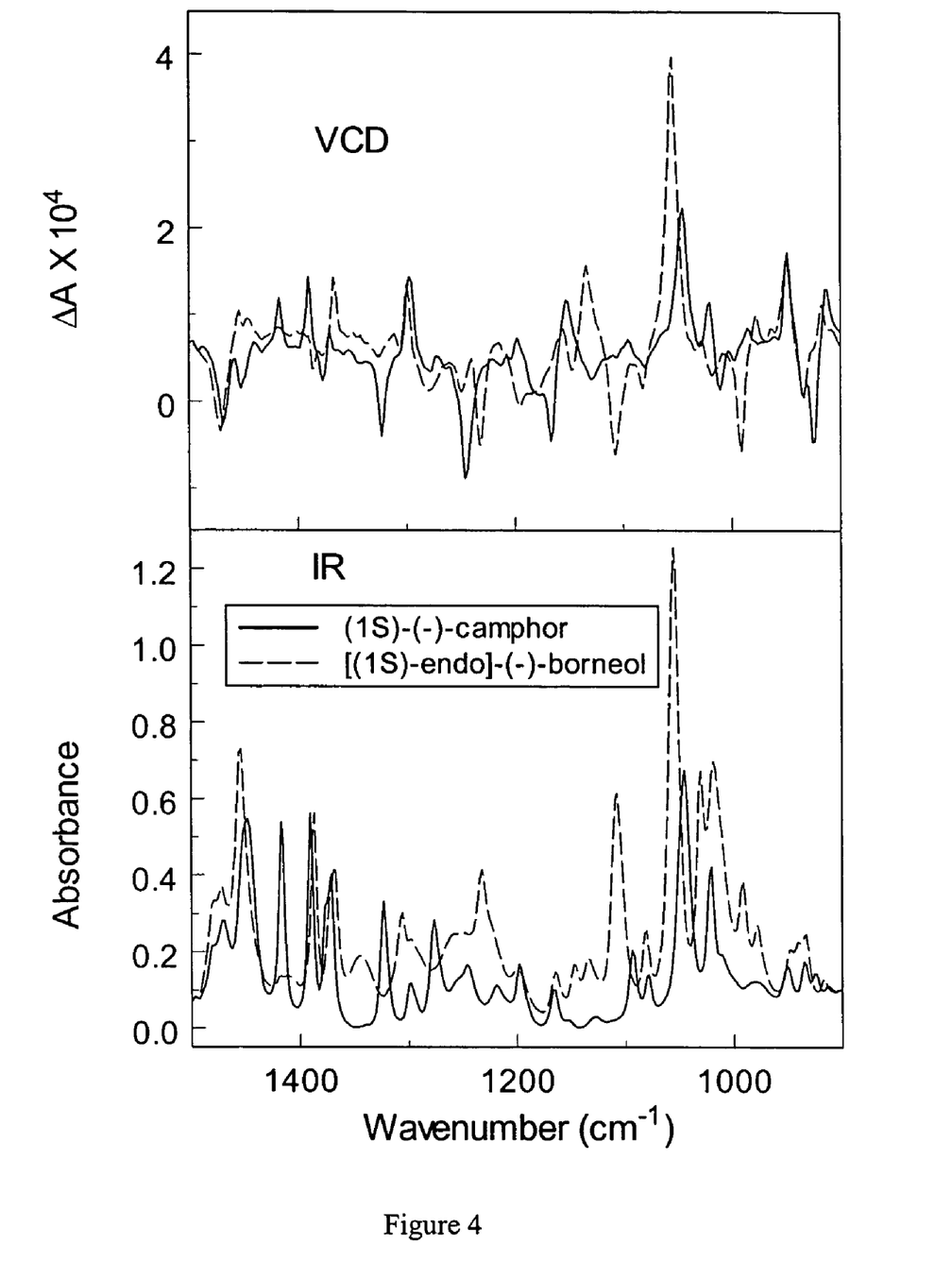
FIG. 4 is plot of the IR and VCD spectra (+)-camphor and (+)-borneol as 1.0M solutions in $CCl_4$.
Figure 5A:
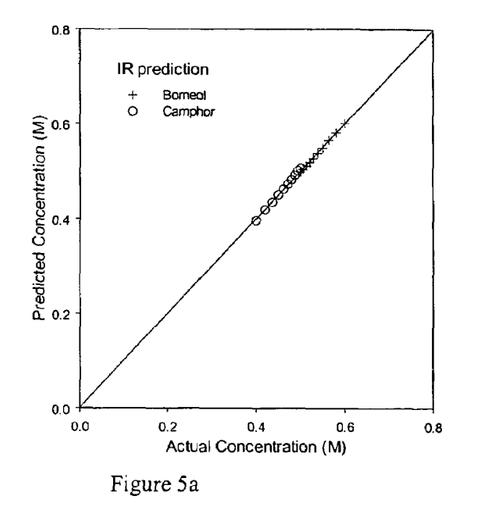
FIG. 5a is a graph showing the predicted versus actual concentration of camphor and borneol using IR spectra to monitor the concentrations.
Figure 5B:
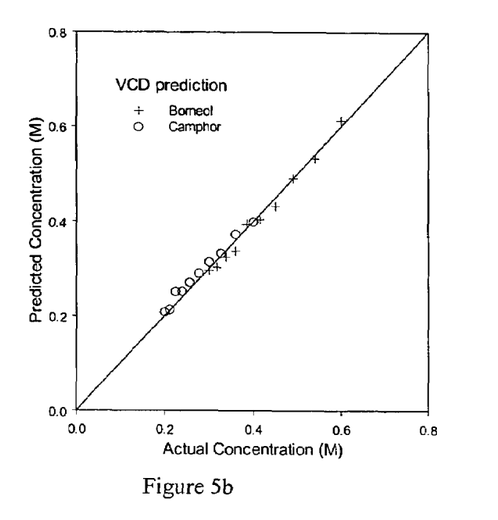
FIG. 5b is a graph showing the predicted apparent versus actual concentrations of camphor and borneol using VCD spectra to monitor the concentrations.
Figure 5C:
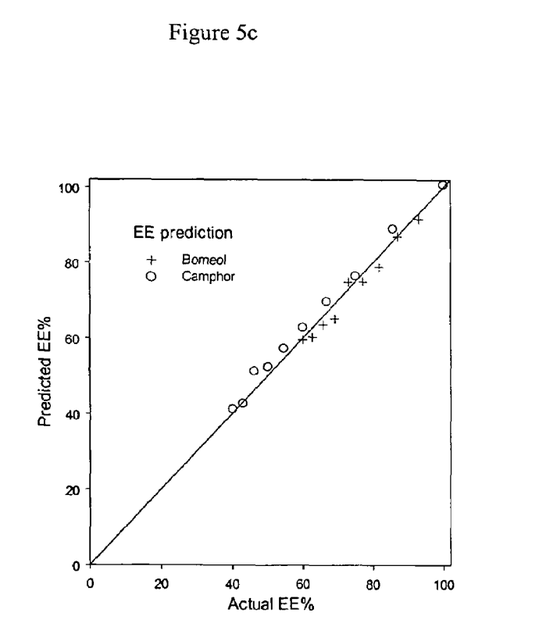
FIG. 5c is a graph showing the predicted versus actual % EE of camphor and borneol using VCD spectra normalized by the IR spectra.
Figure 6:
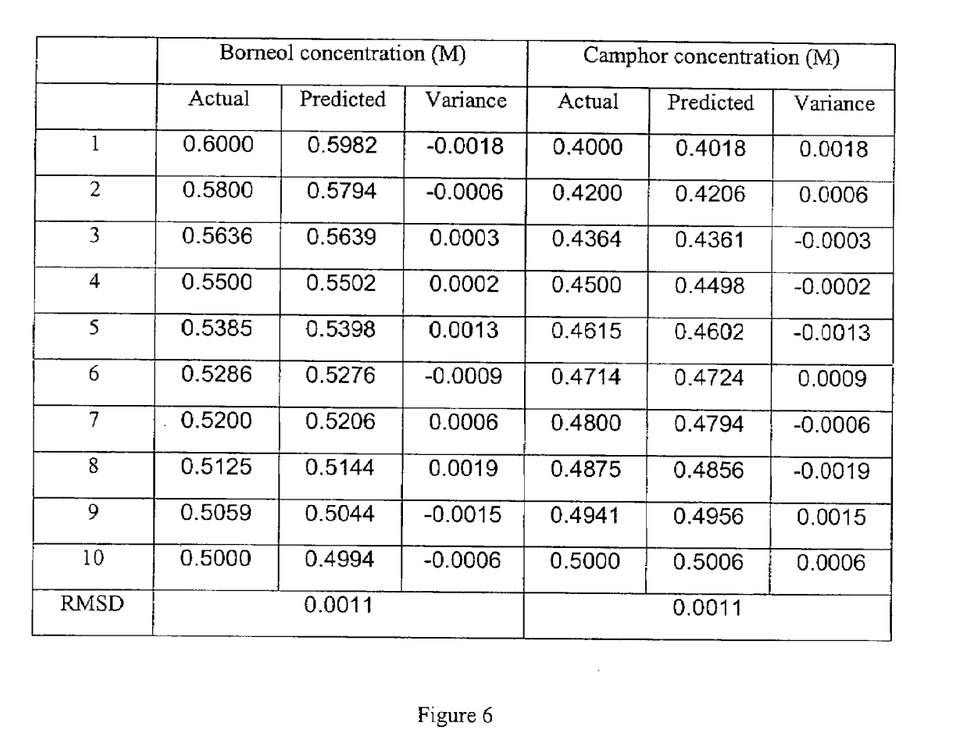
Figure 7:
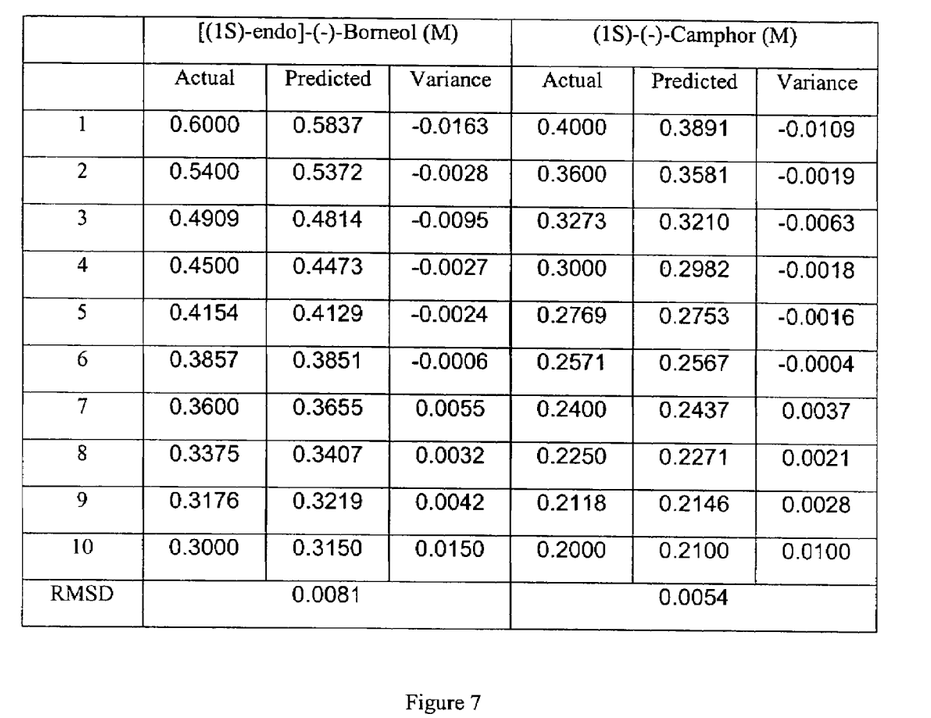
FIG. 7 is a table showing the data used to construct the graph of FIG. 5b.
Figure 8:
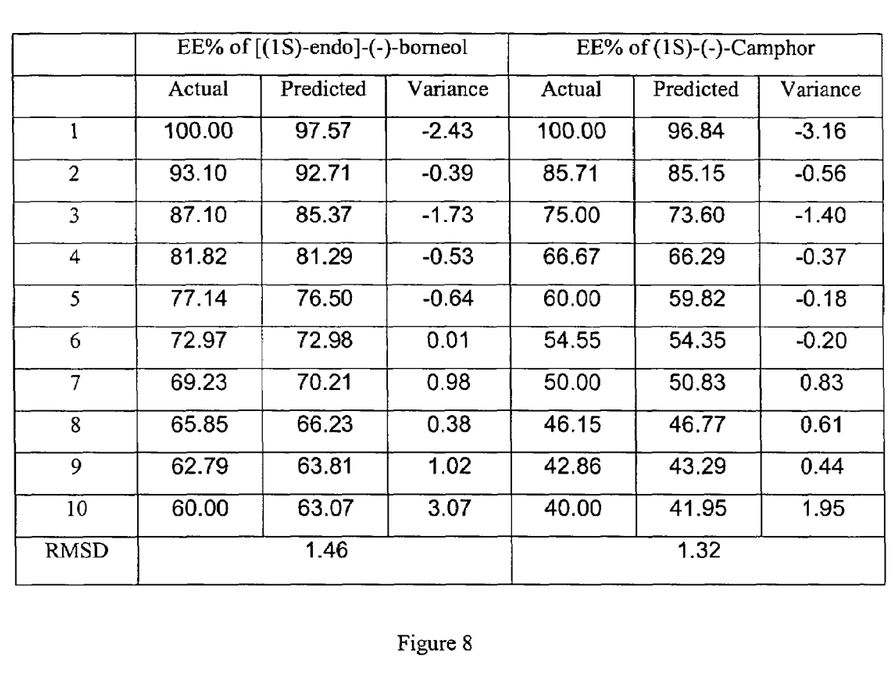
FIG. 8 is a table showing the data used to construct the graph of FIG. 5c.

If we refer back to equation 1 at this point, we can see that the denominator of the calculation to determine % EE is the concentration of the compound present in the solution. That concentration, represented in the equation by ($N_A+N_B$), can be determined from the IR spectrum by itself because the IR spectrum is directly related to the concentration of the compound. If there is no change in concentration, the % EE can be determined from the analysis of the VCD spectra alone, as has been shown in the previous example. It is important that these two entities can be independently determined because in more complex reactions in which a compound is chemically reacted to form another compound, both the concentration of the compound and the % EE could change, in which case the VCD spectra alone is not sufficient to determine % EE. In FIG. 4, a plot of IR and VCD spectra are presented for 1.0M solutions of (+)-camphor and (+)-borneol in $CCl_4$. In FIG. 5, plots are shown that demonstrate the determination of % EE for a mixture of these two species when their concentrations are also changing. Here in the first plot (top left, FIG. 5a), the IR alone was used to monitor the concentration. The second plot (top right, FIG. 5b) shows the apparent concentrations of camphor and borneol obtained from analysis of the composite VCD, but these apparent values are diminished by the % EE values, which are also changing for these two species. When the apparent concentration coefficients from VCD spectra are divided by the actual concentration coefficients obtained from the IR spectra, the changes in % EE of two molecules in the solution are determined as shown in the third plot (bottom center, FIG. 5c). FIGS. 6, 7 and 8 show tables of the numerical data used to construct the three plots in FIG. 5. In spite of the increased complexity of this experiment, it was possible to achieve root-mean-squares deviation of less than 1.5% for % EE of both compounds present when analyzed by the PLS method. Thus the method would have the requisite accuracy to monitor the reaction kinetics of bimolecular reactions.

The invention described herein allows one to simultaneously monitor both the concentration and % EE of multiple chiral species by using a combination of FT-IR and FT-VCD spectrometry with a PLS analysis system. For measurements of absolute % EE values rather than just relative % EE values, calibration with a pure or nearly pure enantiomer of each compound must be undertaken to obtain a VCD spectrum of the species. Given these preliminary calibrations, reaction kinetics can be accurately followed in real time by simultaneous time-dependent measurement of FT-IR and FT-VCD spectra. For measurements of relative % EE, there is no need for prior calibrations, and thus reactions can also be monitored in real-time.

Although experiments carried out here used a flow cell system in a FT-VCD instrument, a fiber-optic sampling system could have been used. Fiber optics have been adapted in the prior art to collect FT-MIR and FT-NIR absorption information for a chemical reaction in a container. The extension of this art to monitoring % EE is not obvious because of problems associated with the control of circular polarization through the fibers. These can be overcome in two basic ways. One way is to use fibers to deliver the infrared radiation from the spectrometer 4 to the reaction vessel prior to linear polarization 6 and circular polarization modulation 8 of the beam, making this only a means of brining the radiation to the flow-cell area and sampling in the usual way. Such a fiber-optic system allows the light to be positioned where it needs to be to collect data about the sample at-line or on-line and one does not need to transport the sample to the spectrometer sample compartment. A second method that can be envisioned with the FT-IR/FT-VCD methods described above is to place the fiber optics after the polarization modulator 8 and allow the fiber optics to deliver circular polarization modulated light directly into the reaction vessel and to collect the raw CD spectrum and return the beam to the detector 12 by fiber optics, thus eliminating the need for a sample flow cell, 10. In either case, fiber optics can be used in a central way to implement the measurement in real time of the composition and % EE of all chiral species participating in chemical reaction.

The detailed description of the preferred embodiment is meant only as an example, and is not meant to encompass the scope of the invention described herein.

What is claimed is:

1. A system for monitoring enantiomeric excess of a plurality of chiral molecules participating in a chemical reaction comprising:
    a means for obtaining a plurality of Fourier transform vibrational circular dichroism spectra and Fourier transform absorption spectra in the mid infrared region of a chemical solution when a chemical reaction is occurring in said chemical solution;
    a means for ordering said plurality of Fourier transform vibrational circular dichroism and absorption spectra as a function of time of collection of spectra;
    a means for analyzing said Fourier transform vibrational circular dichroism spectra and absorption to determine simultaneously the concentration and enantiomeric excess of each chiral molecule as a function of time.

2. A system as claimed in claim 1 wherein said chemical solution is monitored by means of a flow cell.

3. A system as claimed in claim 1 wherein said chemical solution is monitored by means of a fiber-optically-coupled accessory with or without a flow cell.

4. A system for monitoring enantiomeric excess of a plurality of chiral molecules participating in a chemical reaction comprising:
    a means for obtaining a plurality of Fourier transform vibrational circular dichroism spectra and Fourier transform absorption spectra in the near infrared region of a chemical solution when a chemical reaction is ocurring in said chemical solution;
    a means for ordering said plurality of Fourier transform vibrational circular dichroism and absorption spectra as a function of time of collection of spectra;
    a means for analyzing said Fourier transform vibrational circular dichroism spectra and absorption to determine simultaneously the concentration and enantiomeric excess of each chiral molecule as a function of time.

5. A system as claimed in claim 4 wherein said chemical solution is monitored by means of a flow cell.

6. A system as claimed in claim 4 wherein said chemical solution is monitored by means of a fiber-optically-coupled accessory with or without a flow cell.

7. A method for determining the enantiomeric excess of chiral molecule in a solution having a plurality of molecular species including:
    obtaining a concentration coefficient from an IR spectrum for each molecular species in the solution;
    obtaining the apparent concentration coefficient of the VCD spectrum for each molecular species in the solution, wherein the steps of obtaining an IR spectrum, and/or coefficients, and obtaining a VCD spectrum, and/or coefficients are performed simultaneously;
    for each molecular species present in the solution, dividing the apparent concentration coefficient of the VCD spectrum by the concentration coefficient from IR spectrum to obtain a % EE for each molecular species.

8. The method for monitoring the enantiomeric excess of molecules in a reaction chamber, including:
    providing a reaction chamber to contain the molecules;
    providing an instrument for producing both an IR spectrum and a VCD spectrum of the molecules in the reaction chamber;
    using the instrument to obtain an IR spectrum and the VCD spectrum of the molecules in the reaction chamber;
    obtaining the concentration coefficients of each species from the IR spectrum and the apparent coefficients of each species from the VCD spectrum;
    dividing the apparent concentration coefficient of each species present in the VCD spectrum by the corresponding concentration coefficient of each species in the IR spectrum,
    thereby obtain the % EE VCD of each species present in the reaction chamber during the course of the reaction.

9. The method of claim 8, further including providing a fiberoptic pathway between the reaction chamber and the instrument.

10. The method of claim 9, further including a flow cell connected to the reaction chamber and positioning the instrument for producing both the IR spectrum and the VCD spectrum in proximity to the flow cell, so that the spectra are produced by sampling the molecules in the flow cell.

11. The method of claim 10, wherein the temperature of the reaction chamber environment is controllable, and wherein the % EE information for a particular molecule of interest is used to control the temperature, pressure or other.

12. The system of claim 9, wherein the fiberoptic pathway between the reaction chamber and the instrument delivers infrared radiation to the reaction chamber prior to linear polarization and circular polarization by the instrument.

13. The system of claim 9, wherein the fiberoptic pathway is disposed after a polarization modulator.

14. The method of claim 8, further including providing concentration coefficients from the IR spectrum and apparent concentration coefficients of the VCD spectrum of a molecule of interest and the step of determining the % EE of a molecule of interest by dividing the VCD and IR concentration coefficients.

15. The method of claim 14, further including using a partial least squares analysis to determine the concentration coefficients of the IR spectrum and the apparent concentration coefficients of the VCD spectrum by comparison to the IR spectrum and the VCD spectrum of the molecule at known concentrations.

* * * * *